(12) United States Patent
Ueda et al.

(10) Patent No.: US 9,924,962 B2
(45) Date of Patent: Mar. 27, 2018

(54) ELBOW JOINT SURGICAL TREATMENT

(71) Applicant: OLYMPUS CORPORATION, Tokyo (JP)

(72) Inventors: Sohei Ueda, Tokyo (JP); Chie Onuma, Tama (JP); Manabu Ishikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 342 days.

(21) Appl. No.: 14/878,577

(22) Filed: Oct. 8, 2015

(65) Prior Publication Data
US 2017/0100154 A1 Apr. 13, 2017

(51) Int. Cl.
A61B 17/32 (2006.01)
A61B 90/00 (2016.01)
A61B 17/16 (2006.01)

(52) U.S. Cl.
CPC ........... *A61B 17/320068* (2013.01); *A61B 17/320016* (2013.01); *A61B 17/16* (2013.01); *A61B 90/361* (2016.02); *A61B 90/37* (2016.02); *A61B 2017/32007* (2017.08); *A61B 2017/320008* (2013.01); *A61B 2017/320069* (2017.08); *A61B 2017/320073* (2017.08); *A61B 2217/005* (2013.01); *A61B 2217/007* (2013.01)

(58) Field of Classification Search
CPC ............................................. A61B 17/320068
See application file for complete search history.

(56) References Cited

U.S. PATENT DOCUMENTS

| | | |
|---|---|---|
| 6,544,260 B1 | 4/2003 | Markel et al. |
| 8,709,089 B2 | 4/2014 | Lang et al. |
| 2004/0068267 A1 | 4/2004 | Harvie et al. |
| 2005/0054954 A1 | 3/2005 | Lidgren et al. |
| 2006/0030871 A1 | 2/2006 | Hain et al. |
| 2010/0121197 A1 | 5/2010 | Ota et al. |
| 2010/0174368 A1 | 7/2010 | Lynch et al. |
| 2010/0191173 A1 | 7/2010 | Kimura et al. |
| 2010/0298894 A1 | 11/2010 | Bojarski et al. |
| 2010/0312350 A1 | 12/2010 | Bonutti |
| 2011/0196401 A1 | 8/2011 | Robertson et al. |
| 2012/0165843 A1 | 6/2012 | Gannoe et al. |
| 2013/0096471 A1 | 4/2013 | Slayton et al. |
| 2015/0165243 A1 | 6/2015 | Slayton et al. |

FOREIGN PATENT DOCUMENTS

| | | |
|---|---|---|
| JP | H05-168642 A | 7/1993 |
| JP | 2006-334268 A | 12/2006 |

*Primary Examiner* — Andrew Yang
(74) *Attorney, Agent, or Firm* — Oliff PLC

(57) ABSTRACT

An elbow joint surgical treatment includes transmitting an ultrasonic vibration to a treating portion of an ultrasonic device to excise the treated object region of the synovial membrane, and bringing the treating portion of the ultrasonic device, used in excising the synovial membrane, to come in contact with an osteophyte positioned in one of a coronoid fossa of a humerus, an olecranon fossa of the humerus, a coronoid process of an ulna, and an olecranon. The surgical treatment includes transmitting an ultrasonic vibration to the treating portion in contact with the osteophyte to remove the osteophyte.

3 Claims, 8 Drawing Sheets

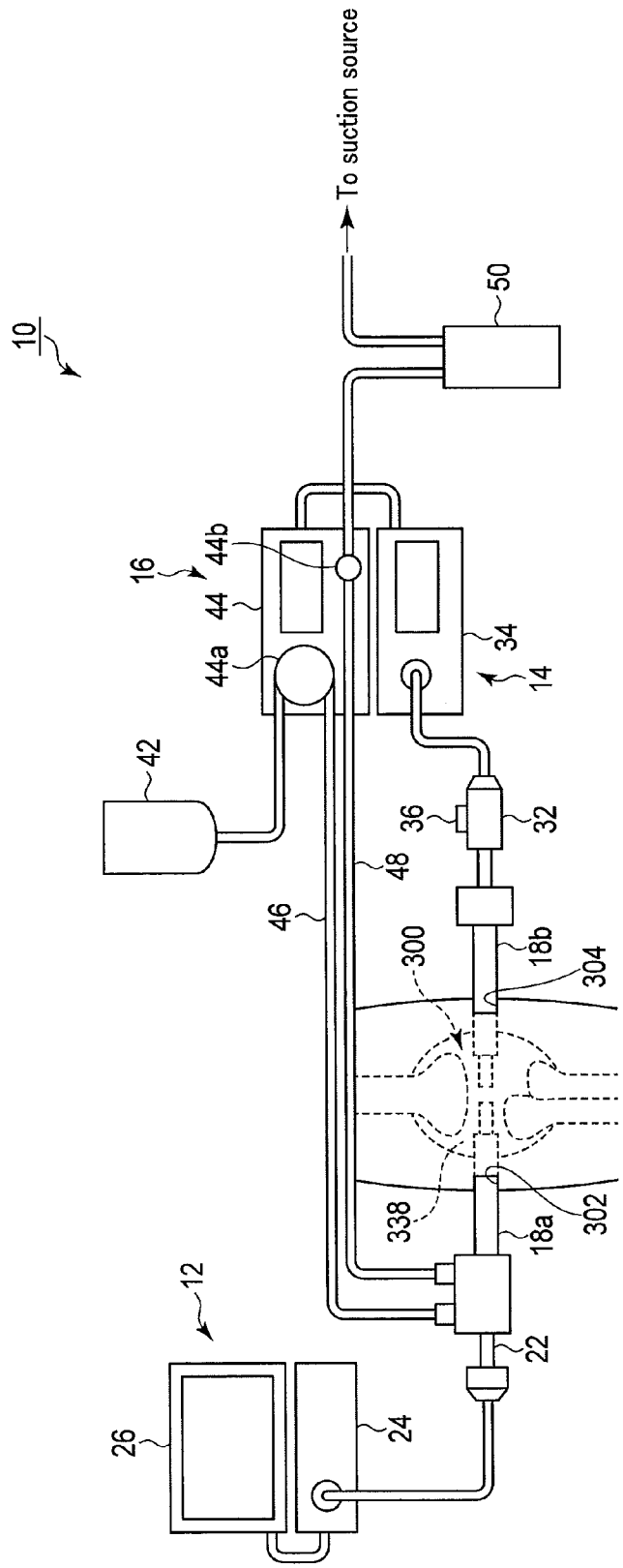
F I G. 1

ELBOW JOINT SURGICAL TREATMENT

BACKGROUND OF THE INVENTION

1. Field of the Invention

The present invention relates to an elbow joint surgical treatment to be performed under an arthroscope.

2. Description of the Related Art

It is known that, when performing an arthroscopic surgical treatment for a patient's elbow joint, a surgeon proceeds with the treatment while inserting and removing each of treatment tools through a portal many times in accordance with a tissue of a treated region, and the above treatment tools are, for example, a shaver to shave a soft tissue, an abrader burr to abrade a bone, or an RF device to excise the soft tissue while stopping bleeding.

BRIEF SUMMARY OF THE INVENTION

According to one aspect of the invention, An elbow joint surgical treatment which is to be performed under an arthroscope, the surgical treatment including: inserting the arthroscope and a treating portion of an ultrasonic device into an elbow joint; excising a treated object region of a synovial membrane by transmitting an ultrasonic vibration to the treating portion in a state where the treating portion is in contact with the treated object region of the synovial membrane while observing the treating portion of the ultrasonic device and the treated object region of the synovial membrane with the arthroscope; bringing the treating portion of the ultrasonic device, used in excising the treated object region of the synovial membrane, to approach and come in contact with an osteophyte that is a treated object region positioned in one of a coronoid fossa of a humerus, an olecranon fossa of the humerus, a coronoid process of an ulna, and an olecranon; and removing the osteophyte by transmitting an ultrasonic vibration to the treating portion of the ultrasonic device in a state where the treating portion is in contact with the osteophyte while observing the treating portion and the osteophyte with the arthroscope.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a treatment system for use in an elbow joint surgical treatment;

DETAILED DESCRIPTION OF THE INVENTION

First Embodiment

Figure 2:
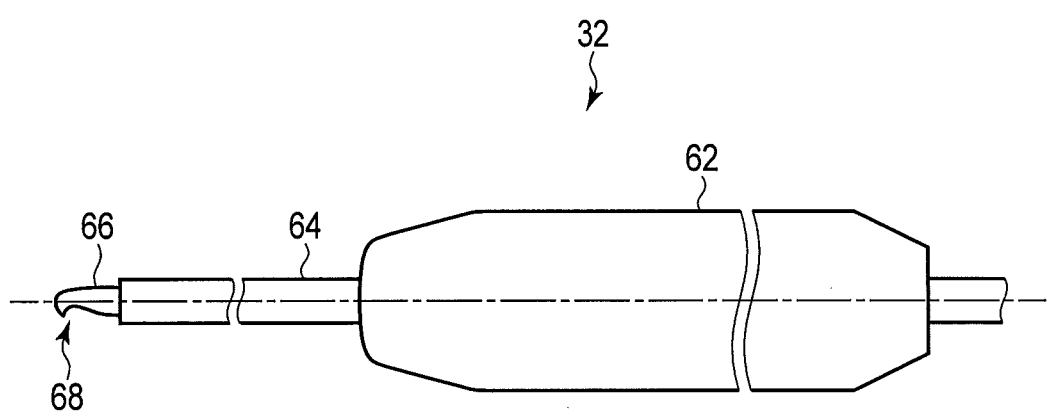
FIG. 2 is a schematic view showing one example of an ultrasonic treatment tool of the treatment system for use in the elbow joint surgical treatment.

A first embodiment according to the present invention will now be described with reference to FIG. 1 to FIG. 11C.

When an elbow joint 300 is treated, for example, a treatment system 10 shown in FIG. 1 is used. The treatment system 10 includes an arthroscope device 12, a treatment device 14, and a perfusion device 16.

The arthroscope device 12 includes an arthroscope 22 configured to observe an inner part of the elbow joint 300, i.e., the inside of a joint cavity 338 of a patient, an arthroscope controller 24 configured to perform image processing on the basis of a subject image imaged by the arthroscope 22, and a monitor 26 configured to display the image generated by the image processing in the arthroscope controller 24. The arthroscope 22 is inserted into the joint cavity 338 of the elbow joint 300 through a first cannula 18a that forms a portal 302 via which the inner side of the elbow joint 300 of the patient communicates with an outer side of skin. The treatment device 14 includes an ultrasonic treatment tool 32, a treatment tool controller 34, and a switch 36. Here, the treatment tool controller 34 supplies energy to the ultrasonic treatment tool 32 in accordance with an operation of the switch 36 to transmit an ultrasonic vibration to a treating portion (end effector) 68 of an after-mentioned probe 66 of the ultrasonic treatment tool 32. The treatment tool 32 is inserted into the joint cavity 338 of the elbow joint 300 through a second cannula 18*b* that forms a portal 304 via which the inner side of the elbow joint 300 of the patient communicates with the outer side of the skin. It is to be noted that the switch 36 maintains, for example, a driven state of an ultrasonic transducer in a state where the switch is pressed to be operated, and when the pressed state is released, the driven state of the ultrasonic transducer is released.

Here, it is described that the one switch 36 is disposed, but the switches may be disposed. An amplitude of the ultrasonic transducer can suitably be set by the treatment tool controller 34. In consequence, by the operation of the switch 36, a frequency of the ultrasonic vibration to be output from the after-mentioned ultrasonic transducer is the same, but the amplitude may be different. Therefore, the switch 36 can suitably switch the amplitude of the ultrasonic transducer to states such as two large and small states. For example, when the amplitude can be switched to the two large and small states, the ultrasonic vibration of the small amplitude is for use in treating comparatively soft tissues such as a synovial membrane 337, and cartilages 312*a*, 314*a* and 316*a*. The ultrasonic vibration of the large amplitude is for use in treating comparatively hard tissues such as bones (a humerus 312, and an ulna 314).

It is to be noted that, for example, the two switches 36 may be disposed in parallel, or a hand switch and a foot switch may selectively be used. Additionally, when the one switch 36 is switched to be used, the ultrasonic vibration of the small amplitude may be output by one operation, and the ultrasonic vibration of the large amplitude may be output by two quick pressing operations as in a double click operation of a mouse for a computer.

The perfusion device 16 includes a bag-shaped liquid source 42 that contains a perfusion liquid such as physiological saline, a perfusion pump unit 44, a liquid supply tube 46 whose one end is connected to the liquid source 42, a liquid discharge tube 48, and a suction bottle 50 to which one end of the liquid discharge tube 48 is connected. The suction bottle 50 is connected to a suction source attached to a wall of an operating room. In the perfusion pump unit 44, the perfusion liquid can be supplied from the liquid source 42 by a liquid supply pump 44*a*. Additionally, in the perfusion pump unit 44, suction/suction stop of the perfusion liquid in the joint cavity 338 of the elbow joint 300 to the suction bottle 50 can be switched by opening/closing a pinching valve 44*b* as a liquid discharge valve.

The other end of the liquid supply tube 46 that is a liquid supply donduit is connected to the first cannula 18*a*. In consequence, the perfusion liquid can be supplied into the joint cavity 338 of the elbow joint 300 via the first cannula 18*a*. The other end of the liquid discharge tube 48 that is a liquid discharge conduit is connected to the first cannula 18*a*. In consequence, the perfusion liquid can be discharged from the joint cavity 338 of the elbow joint 300 via the first cannula 18*a*. It is to be noted that, needless to say, the other end of the liquid discharge tube 48 may be connected to the second cannula 18*b*, so that the perfusion liquid can be discharged from the elbow joint 300.

It is to be noted that, here, the perfusion liquid can be supplied and discharged through the first cannula 18*a*, but a function that is capable of supplying and/or discharging the perfusion liquid may be imparted to, for example, the arthroscope 22. Similarly, the function that is capable of supplying and/or discharging the perfusion liquid may be imparted to the ultrasonic treatment tool 32. In addition, a function that is capable of supplying and discharging the perfusion liquid through the second cannula 18*b* may be imparted. Furthermore, the perfusion liquid may be supplied and discharged through a separate portal.

As shown in FIG. 2, the ultrasonic treatment tool 32 has a housing 62, a sheath 64 projected from the housing 62, and the probe 66 inserted through the sheath 64. In particular, outer peripheral surfaces of the housing 62 and the sheath 64 have insulating properties. The probe 66 is made of a metal material such as a titan alloy material capable of transmitting the ultrasonic vibration. To a proximal end of the probe 66, an unshown ultrasonic transducer unit which disposed in the housing 62 is fixed. In the ultrasonic treatment tool 32, the treating portion 68 of the probe 66 inserted through the sheath 64 is disposed together with the sheath 64 in the joint cavity 338 through the second cannula 18*b*. Further, when the switch 36 is pressed, energy is supplied from the treatment tool controller 34 to the ultrasonic transducer unit fixed to the proximal end of the probe 66, and the ultrasonic vibration is generated in the ultrasonic transducer. This generated ultrasonic vibration is transmitted from the proximal end of the probe 66 toward a distal side, and hence with the aid of the treating portion 68 provided in a distal portion of the probe 66, the hard tissue (the bone tissue or the like) can be resected and the soft tissue (the cartilage, a membrane tissue or the like) can be excised.

It is to be noted that a shape of the treating portion 68 can suitably be selected in accordance with a treated region. Here, there is described an example where a hook type of treating portion shown in FIG. 2 is used, but various shapes such as a rake type, a blade type and a curette type can selectively be used in consideration of an accessibility to the treated region, or an adaptability to the treatment on the basis of a position, a shape, a size or the like of a cutting portion of the treating portion 68. In addition, the treating portion 68 may have a constitution where a groove is formed in a crosshatched state, or a constitution where grooves are disposed in parallel in the treating portion 68 in an extending direction of the probe 66 and each of the grooves is extended substantially perpendicular to the extending direction of the probe 66.

Figure 3:
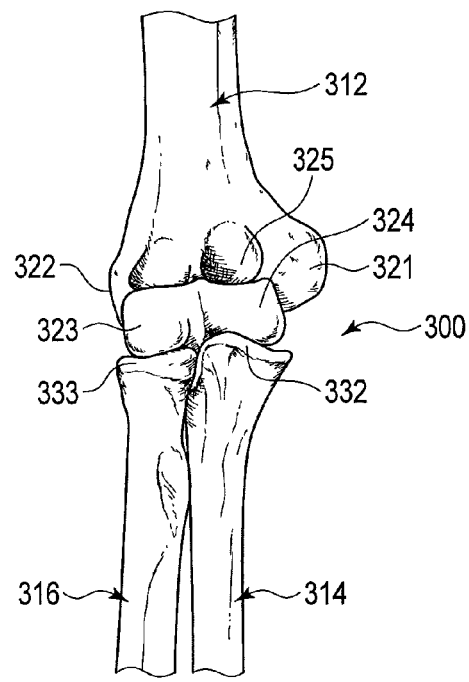
FIG. 3 is a schematic view of a right elbow joint seen from an anterior side of a human body.
Figure 4:
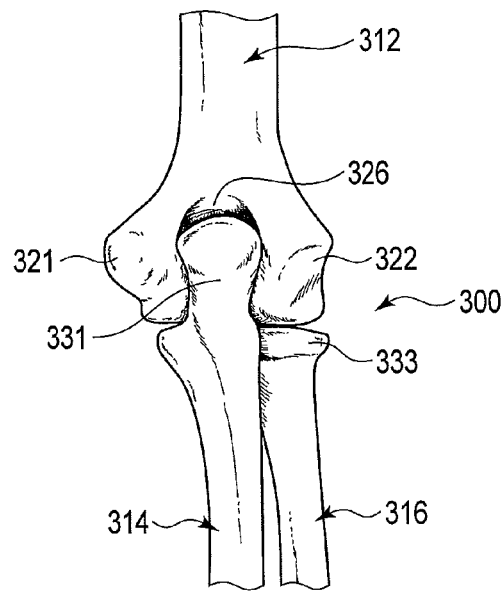
FIG. 4 is a schematic view of the right elbow joint seen from a posterior side (a rear side) of the human body.
Figure 5:
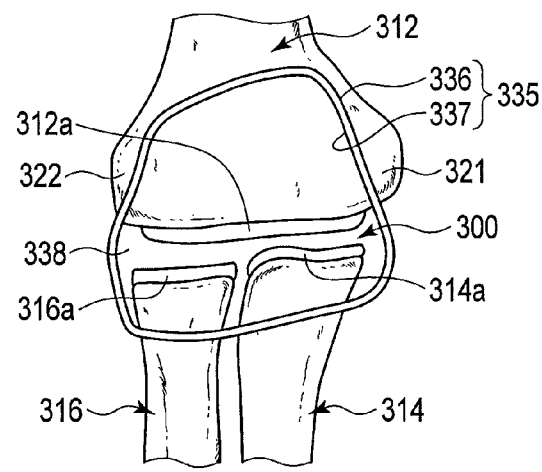
FIG. 5 is a schematic view schematically showing the right elbow joint together with the articular capsule.

A structure of the elbow joint 300 will briefly be described. FIG. 3 to FIG. 5 are views showing the elbow joint 300. FIG. 3 shows a case where the right elbow joint 300 is seen from an anterior side of a human body (in a stretching posture on a front side), and FIG. 4 shows a case where the right elbow joint 300 is seen from a posterior side of the human body (in the stretching posture on a rear side). Additionally, FIG. 5 is a view schematically showing the right elbow joint 300 together with an after-mentioned joint capsule 335 and the cartilages 312*a*, 314*a* and 316*a*. As shown in FIG. 3 to FIG. 5, the elbow joint 300 is a joint formed of the humerus 312, the ulna 314, and a radius 316.

As shown in FIG. 3 and FIG. 4, the humerus 312 has a medial epicondyle 321, a lateral epicondyle 322, a capitulum 323 of the humerus, a trochlea 324 of the humerus, a coronoid fossa 325, and an olecranon fossa 326 on an elbow joint 300 side. Additionally, the ulna 314 has an olecranon 331 and a coronoid process 332 on the elbow joint 300 side. Further, the radius 316 has a radial head 333 on the elbow joint 300 side.

As shown in FIG. 5, the elbow joint 300 is encapsulated in the joint capsule 335. The joint capsule 335 is formed of an outer fibrous tunica 336 and the inner synovial membrane 337. The synovial membrane 337 forms pleats and secretes a synovial fluid, and hence the elbow joint 300 smoothly moves. The inside of the joint capsule 335 is called the joint cavity 338, and the joint cavity 338 is filled with the synovial fluid to be secreted from the synovial membrane 337. The joint cavity 338 of the elbow joint 300 is incompletely divided into two anterior and posterior cavities.

Additionally, in the elbow joint 300, each of the cartilages (the joint cartilages) 312a, 314a and 316a is present between the bones (the humerus 312, the ulna 314 and the radius 316). The cartilage 312a is disposed on an inferior surface of the humerus 312. Further, the cartilage 314a is disposed on a superior surface of the ulna 314, and the cartilage 316a is disposed on a superior surface of the radius 316. The cartilages 312a, 314a and 316a can absorb impact in the elbow joint 300 and smoothen movement of the elbow joint 300.

Figure 6:
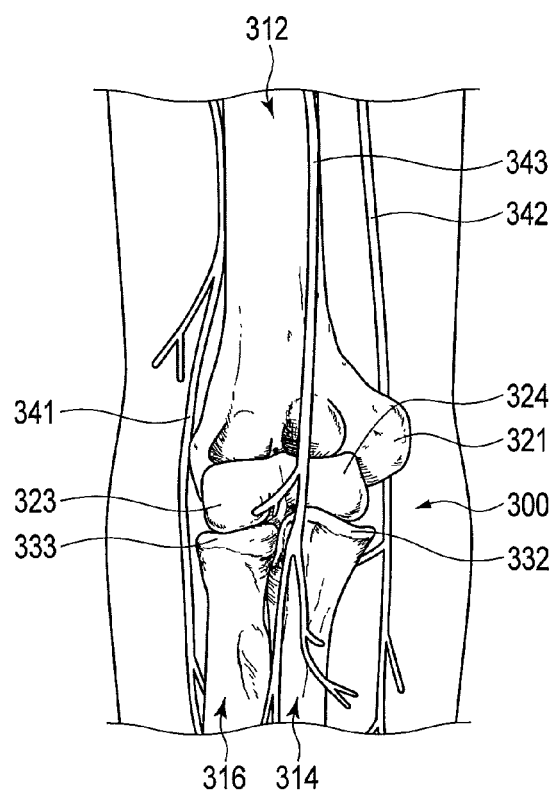
FIG. 6 is a schematic view showing running of nerves in the right elbow joint and the vicinity of the right elbow joint.

FIG. 6 is a view showing running of nerves in the elbow joint 300 and the vicinity of the elbow joint. As shown in FIG. 6, a lot of nerves run in the vicinity of the elbow joint 300. For example, a radial nerve 341 runs toward inferior along a posterior surface of the humerus 312, reaches anterior surfaces of the humerus capitulum 323 and the radial head 333, and runs on a lateral side along the radius 316. Additionally, an ulnar nerve 342 passes through a rear side of the medial epicondyle 321 of the humerus 312, and runs on a medial side along the ulna 314. In addition, a median nerve 343 runs down on a medial side of the humerus 312, and reaches anterior sides of the humerus trochlea 324 and the coronoid process 332 of the ulna 314.

Next, there will be described a method of performing a surgical treatment of removing an osteophyte 345 in the humerus 312 or the ulna 314 of the elbow joint 300. In particular, there will be described a surgical treatment of removing the bone spur 345 formed in one of the coronoid fossa 325 of the humerus 312, the olecranon fossa 326 of the humerus 312, the coronoid process 332 of the ulna 314, and the olecranon 331.

For example, when a pitching action is repeatedly performed in baseball, a trouble of a so-called little league elbow occurs in the elbow joint 300. As one of symptoms of the little league elbow, the osteophyte 345 might be formed in one of the coronoid fossa 325, the olecranon fossa 326, the coronoid process 332, and the olecranon 331. The bone spur 345 is formed in one of the coronoid fossa 325, the olecranon fossa 326, and the coronoid process 332, and hence a joint movement is obstructed. In addition, when the symptom of the little league elbow or the like proceeds, osteoarthritis of an elbow might be caused. In this case, there is a possibility that the synovial membrane 337 causes inflammation and is thickened.

In the surgical treatment, a condition of the elbow joint 300 is confirmed by using an X-ray, MRI or the like. When the osteophyte 345 is confirmed in one of the coronoid fossa 325, the olecranon fossa 326, the olecranon 331 and the coronoid process 332, a position or the like of the osteophyte 345 is confirmed in advance.

Further, an instrument to form the portals 302 and 304 in the elbow joint 300, and an instrument for use in the surgical treatment of removing the osteophyte 345 are prepared. It is to be noted that the treating portion 68 of the ultrasonic treatment tool 32 is formed into a suitable shape such as the hook type.

Further, a surgeon forms the portal 302 for the patient who bends the elbow joint 300 of the right elbow (may be a left elbow). When necessary, the first cannula 18a is disposed in the portal 302. A distal end of the arthroscope 22 is disposed in the joint cavity 338 of the elbow joint 300 through the first cannula 18a. Here, the first cannula 18a is not necessarily required, when the perfusion device 16 is connectable to the arthroscope 22.

Additionally, in the vicinity of the elbow joint 300, a lot of nerves (the radial nerve 341, the ulnar nerve 342, the median nerve 343, etc.) run. Therefore, it is necessary to form the portal 302 without damaging the nerves. Therefore, as the portal 302, there is employed one of a proximal anterolateral portal, a distal anterolateral portal, a direct lateral portal, an anteromedial portal, a proximal medial portal, a straight posterior portal and a posterolateral portal. It is determined which one of the abovementioned portals is to be employed as the portal 302, on the basis of the position of the osteophyte 345 to be removed (i.e., a position of a treated object region).

When the distal end of the arthroscope 22 is disposed in the joint cavity 338, the joint cavity 338 of the elbow joint 300 is filled with physiological saline by use of the perfusion device 16. In this state, the inside of the joint cavity 338 of the elbow joint 300 is suitably observed by using the arthroscope 22. Further, one of the coronoid fossa 325, the olecranon fossa 326 and the coronoid process 332 is in a view field of the arthroscope 22 to confirm the position of the osteophyte 345. In addition, an inflamed condition of the synovial membrane 337 on the inner side of the joint capsule 335 of the elbow joint 300 is confirmed.

Further, the surgeon forms the portal 304 for the patient who bends the elbow joint 300. When necessary, the second cannula 18b is disposed in the portal 304. The treating portion 68 of the ultrasonic treatment tool 32 is disposed in the joint cavity 338 of the elbow joint 300 through the second cannula 18b. Also as the portal 304, there is employed one of the proximal anterolateral portal, the distal anterolateral, portal, the direct lateral portal, the anteromedial portal, the proximal medial portal, the straight posterior portal and the posterolateral portal which is different from the portal 302. It is also determined which one of the abovementioned portals is to be employed as the portal 304, on the basis of the position of the bone spur 345 to be removed (i.e., the position of the treatment object region).

Figure 7:
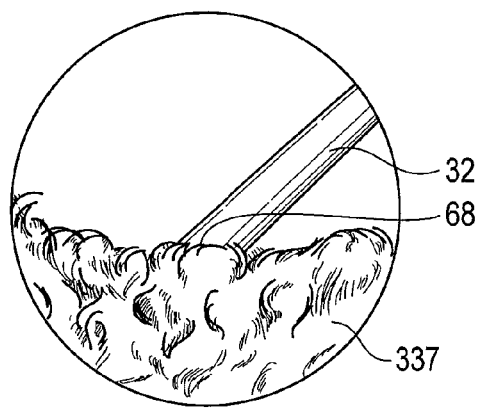
FIG. 7 is a schematic view showing a state where the ultrasonic vibration is transmitted to the treating portion of the ultrasonic treatment tool to excise the synovial membrane in the articular capsule of the elbow joint under the arthroscope.

When the inflamed region is present in the synovial membrane 337 of the joint capsule 335 confirmed with the arthroscope 22, as shown in FIG. 7, the surgeon adjusts the treating portion 68 of the ultrasonic treatment tool 32 to approach the inflamed region (the treated object region) while observing the inflamed region with the arthroscope 22. Further, the surgeon operates the switch 36 of the treatment device 14 to generate the ultrasonic vibration of the suitable amplitude in the ultrasonic transducer, thereby only moving the treating portion 68 in an axial direction of the probe 66, whereby the inflamed region of the synovial membrane 337 or an inflamed synovial membrane is excised with the treating portion 68 to which the vibration is transmitted. The excised inflamed region of the synovial membrane 337 is flown with momentum in excising the region. In this case, the surgeon suitably moves the ultrasonic treatment tool 32 and also suitably moves the arthroscope 22 to excise the inflamed region of the synovial membrane 337 or the inflamed synovial membrane pleats with the treating portion 68 of the ultrasonic treatment tool 32 while always disposing the treating portion 68 in the view field of the arthroscope 22. The excised synovial membrane 337 is discharged to the suction bottle 50 through the first cannula 18a and the liquid discharge tube 48.

A head (a treating portion) of an unshown shaver that has heretofore been used in removing the inflamed region of the synovial membrane 337 or the like has a structure to intertwine the inflamed regions by periaxial rotation. Thus, the shaver performs the treatment while intertwining (winding) the inflamed regions, and hence there is a high possibility that the nerves running in the vicinity of the elbow joint 300 are wound during the treatment. In addition, driving force is securely transmitted from a motor of the shaver to the head, and hence it is difficult to form a portion between the motor and the head of the shaver into a suitable shape, and additionally, a head portion of the shaver is formed to be larger than the treating portion 68 of the ultrasonic treatment tool 32. In consequence, it is very difficult for the head portion of the shaver to access the small elbow joint 300. Therefore, even by use of the shaver that has heretofore been used, it might be difficult to remove the synovial membrane 337. Additionally, when the head portion of the shaver becomes larger, it is necessary to use a cannula having a large diameter, and a portal to be formed is also large. Consequently, there is the high possibility that the nerves running in the vicinity of the elbow joint 300 are damaged. On the other hand, when the treatment is performed by using the ultrasonic treatment tool 32, it is not necessary to rotate the treating portion 68. Therefore, damages due to the winding of the nerves running in the vicinity of the elbow joint 300 can be decreased. Additionally, in the case where the treatment is performed by using the ultrasonic treatment tool 32, as compared with the case where the shaver is used, the treating portion 68 can be formed into the suitable shape, and the treating portion 68 can be formed to be smaller, so that a moving range of the treating portion 68 with respect to the second cannula 18*b* can be increased. Therefore, in the case where the ultrasonic treatment tool 32 is used, the elbow joint 300 can more easily be accessed. Consequently, in the case the ultrasonic treatment tool 32 is used, the inflamed region of the synovial membrane 337 can more easily be excised than in the case where the shaver is used. Additionally, when the treating portion 68 is formed to be smaller, the second cannula 18*b* having a small diameter is usable, and hence the portal 304 to be formed can be small. In consequence, the possibility that the nerves are damaged decreases.

Furthermore, as described above, the shaver has the structure to intertwine the inflamed regions of the synovial membrane 337 by the periaxial rotation. Consequently, a force to tear off the synovial membrane 337 acts, and hence bleeding is easily caused. On the other hand, the treating portion 68 of the ultrasonic treatment tool 32 does not periaxially rotate, and the inflamed region can be excised only by moving the treating portion in the axial direction of the probe 66. Further, in the case where the ultrasonic treatment tool 32 is used, the excised region is flown unlike the case where the shaver is used, and hence the view field of the arthroscope 22, especially the view field in the treated object region is easily acquired.

Figure 8A:
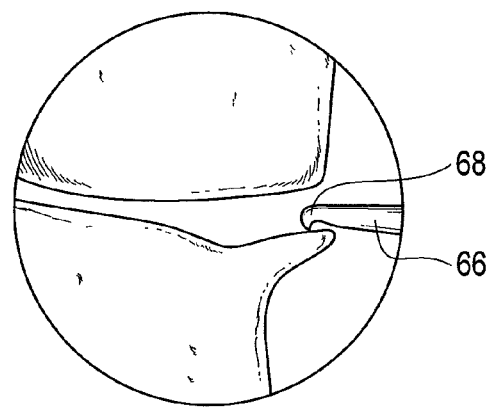
FIG. 8A is a schematic view showing a state where the treating portion of the ultrasonic treatment tool is brought into contact with the bone spur of the elbow joint under the arthroscope.

Further, the surgeon removes the inflamed region of the synovial membrane 337, and then while moving the arthroscope 22 to confirm the inside of the joint cavity 338 of the elbow joint 300, the surgeon moves the ultrasonic treatment tool 32 to bring the treating portion 68 into contact with the osteophyte 345 (the treated object region) to be formed in one of the coronoid fossa 325, the olecranon fossa 326, the coronoid process 332 and the olecranon 331 as shown in FIG. 8A. That is, the same treating portion 68 of the ultrasonic treatment tool 32 as the portion used to excise the synovial membrane 337 is brought into contact with the bone spur 345 without removing out the treating portion from the joint cavity 338 of the elbow joint 300.

Figure 8B:
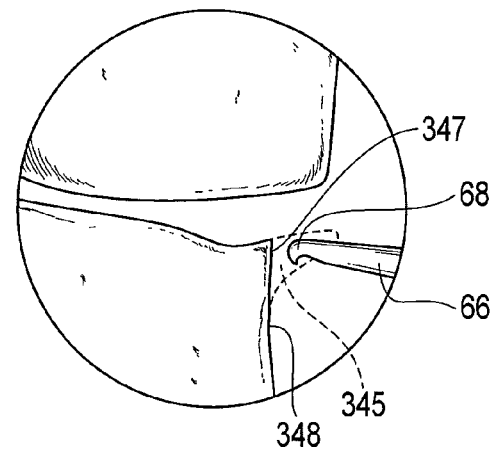
FIG. 8B is a schematic view showing a state where the ultrasonic vibration is transmitted to the treating portion of the ultrasonic treatment tool to remove the bone spur of the elbow joint under the arthroscope.

In the state where the treating portion 68 of the ultrasonic treatment tool 32 is in contact with the osteophyte 345 (the treated object region), the switch 36 is operated to generate the ultrasonic vibration of the suitable amplitude in the ultrasonic transducer. In consequence, the treating portion 68 to which the ultrasonic vibration is transmitted is only moved in the axial direction of the probe 66, to resect the osteophyte 345 formed in the treated object region. When the osteophyte 345 is resected, the osteophyte 345 is removed as shown in FIG. 8B. That is, dissection is performed by the treating portion 68 to which the ultrasonic vibration is transmitted.

An unshown abrader burr that has heretofore been used to resect the bone has a structure to abrade the bone by the periaxial rotation. Therefore, similarly to the abovementioned shaver, a head portion of the abrader burr is formed to be larger (thicker) than the treating portion 68 of the ultrasonic treatment tool 32, and the head portion might have difficulty in accessing a narrow space where the coronoid fossa 325, the olecranon fossa 326, the coronoid process 332 and the olecranon 331 are positioned. Additionally, when the head portion of the abrader burr is large, it is necessary to use a cannula having a large diameter, and a portal to be formed is large. Consequently, there is the high possibility that the nerves running in the vicinity of the elbow joint 300 are damaged. On the other hand, the ultrasonic treatment tool 32 more easily accesses the narrow space where the coronoid fossa 325, the olecranon fossa 326 and coronoid process 332 are positioned than the abrader burr. Consequently, in the case where the treatment is performed by using the ultrasonic treatment tool 32, the osteophyte 345 formed in one of the coronoid fossa 325, the olecranon fossa 326 and the coronoid process 332 can more easily be removed than in the case where the abrader burr is used. Additionally, when the treating portion 68 is small, the second cannula 18*b* having the small diameter is usable, and the portal 304 to be formed is small. In consequence, the possibility that the nerves are damaged decreases.

Additionally, in the case where the abrader burr is used, a cut-off surface is apt to be made fluffy, and hence it is more difficult to smoothen the surface and it is easier to generate concave and convex areas in the excised region. On the other hand, in the case where the treating portion 68 of the ultrasonic treatment tool 32 is used, the precisely and smoothly cut-off surface is more easily formed than in the case where the abrader burr is used. Therefore, in the case where the ultrasonic treatment tool 32 is used, the concave and convex areas of the excised region can be decreased as compared with the case where the abrader burr is used. In consequence, by use of the ultrasonic treatment tool 32, a removed surface 347 from which the osteophyte 345 is removed and a non-removed surface 348 adjacent to the removed surface 347 are smoothly continued.

Additionally, the abrader burr abrades the bone (the osteophyte 345) that is the hard tissue by the periaxial rotation, and hence loads that act on the abrader burr increase in a state where the bone is abraded. Consequently, the whole treatment tool including the abrader burr might noticeably be swung by the loads. The treatment tool to be inserted into the joint cavity 338 of the elbow joint 300 through the portal noticeably swings, and hence there is the high possibility that the nerves running in the vicinity of the elbow joint 300 are damaged. On the other hand, the treating portion 68 of the ultrasonic treatment tool 32 is not periaxially rotated, but the bone can be cut only by moving (vibrating) the treating portion in the axial direction of the probe 66, and hence the loads that act on the treating portion 68 are small in the state where the bone is resected by the treating portion 68. In consequence, there is decreased a possibility that the ultrasonic treatment tool 32 to be inserted into the joint cavity 338 of the elbow joint 300 through the portal 304 noticeably swings, and the possibility that the nerves are damaged decreases. That is, in the state where the bone is resected by the treating portion 68, leaping of the treating portion 68 is not caused by rotary motion unlike in the case of the abrader burr, and hence damages of peripheral tissues (e.g., the nerves) can be decreased.

As described above, the osteophyte 345 formed in one of the coronoid fossa 325, the olecranon fossa 326, the coronoid process 332 and the olecranon 331 is removed, and hence the elbow joint 300 can smoothly be moved. Therefore, the treatment in which the ultrasonic treatment tool 32 is used contributes to a smooth joint movement in the elbow joint 300.

As described above, the osteophyte 345 is removed, the treating portion 68 of the ultrasonic treatment tool 32 is removed out from the second cannula 18b, and the distal end of the arthroscope 22 is pulled out from the first cannula 18a. Furthermore, the first and second cannulas 18a and 18b are removed from the elbow joint 300. Further, the portals 302 and 304 are sutured.

As described above, the technique of removing the osteophyte 345 formed in one of the coronoid fossa 325, the olecranon fossa 326, the coronoid process 332 and the olecranon 331 can be considered as follows.

By use of the treatment system 10, the surgeon can perform a series of treatment of excising the synovial membrane 337 and removing the osteophyte 345 formed in one of the coronoid fossa 325, the olecranon fossa 326, the coronoid process 332 and the olecranon 331 with the treating portion 68 of the treatment tool 32 while the one ultrasonic treatment tool 32 is disposed as it is in the second cannula 18b. Heretofore, the treatment has been performed by replacing different instruments for the portal 304, e.g., using the shaver or the like in excising the synovial membrane 337 that is the soft tissue and using the abrader burr or the like in removing the osteophyte 345 that is the hard tissue, but the treatment can be performed with the one treatment tool 32. In consequence, the surgeon does not have to replace the treatment tool 32 disposed in the joint cavity 338 during the surgical treatment, and hence surgical treatment time can be shortened;

Next, there will be described a method of excising a damaged region of the cartilage under the arthroscope 22. Here, the method of removing the deformed cartilage is only described, but may be performed together with above mentioned excision of the synovial membrane 134 and/or the removing the osteophyte 345 formed in one of the coronoid fossa 325, the olecranon fossa 326, the coronoid process 332 and the olecranon 331. In this case, the excision of the cartilage is performed together with the excision of the synovial membrane 134 and/or the cutting off of the bone spur, without removing the treating portion 68 of the same ultrasonic treatment tool 32 from the joint cavity 338 of the elbow joint 300.

In the elbow joint 300, osteochondritis dissecans (OCD) might be caused by the little league elbow. The osteochondritis dissecans are confirmed using MRI or the like by the surgeon. Degrees of progress of the osteochondritis dissecans are indicated as, for example, grades of ICRS (International Cartilage Repair Society), i.e., Grade 0 (Normal), Grade 1 (Stable, continuity: Softened area covered by intact cartilage), Grade 2 (Partial discontinuity, stable on probing), Grade 3 (Complete discontinuity, "dead in situ", not dislocated), Grade 4 (Dislocated fragment, loose within the bed or empty defect. >10 mm in depth is B-subgroup). In the elbow joint 300, the cartilages 312a are damaged in, for example, the lateral epicondyle 322 of the humerus 312 due to the osteochondritis dissecans.

Further, as like the excision of the synovial membrane 134 and the removing the osteophyte 345, the portal 302 is formed, and a distal end of the arthroscope 22 is disposed in the joint cavity 338 of the elbow joint 300 of the right elbow (may be a left elbow) through the first cannula 18a to be disposed in the portal 302. Additionally, the portal 304 is formed, and the treating portion 68 of the ultrasonic treatment tool 32 is disposed in the joint cavity 338 of the elbow joint 300 through the second cannula 18b to be disposed in the portal 304. In this case, the perfusion device 16 is used to fill the joint cavity 338 of the elbow joint 300 with physiological saline. One of the abovementioned portals is to be employed as each of the portals 302 and 304, and thereby the portals 302a and 304 is formed without damaging the nerves running in the vicinity of the elbow joint 300.

Figure 9:
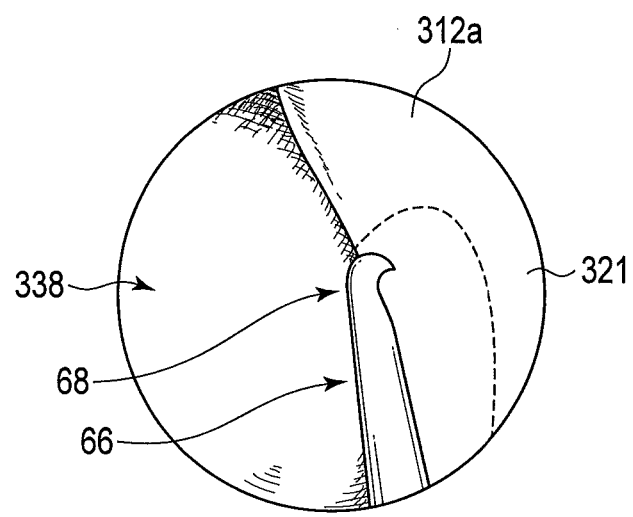
FIG. 9 is a schematic view showing a state where the ultrasonic vibration is transmitted to the treating portion of the ultrasonic treatment tool to remove a treated object region of the cartilage of the elbow joint under the arthroscope.

In a state where the distal end of the arthroscope 22 is disposed in the joint cavity 338, a condition of the cartilage in the joint cavity 338 of the elbow joint 300 is observed. For example, when the cartilage 312a adhered to the lateral epicondyle 322 of the humerus 312 is damaged, the surgeon confirms the grade of the osteochondritis dissecans with the arthroscope 22. By use of the arthroscope 22, the surgeon confirms whether a part of the cartilage 312a is softened (Grade 1), whether laceration such as partial tear is present in a part of the cartilage 312a (Grade 2), whether a part of the cartilage 312a is discontinued from a bone (the lateral epicondyle 322 of the humerus 312) to which the cartilage 312a adheres (Grade 3), or whether a bone cartilage piece is liberated and the bone (the lateral condyle 322 of the humerus 312) having been hidden behind the cartilage 312a is exposed (Grade 4), to judge the grade. Additionally, in each of Grades 1 to 4, presence/absence of the bone spurs is confirmed in the lateral epicondyle 322 of the humerus 312. Further, as shown in FIG. 9, the treating portion 68 of the ultrasonic treatment tool 32 is brought into contact with the treatment object region while observing the treated object region always disposed in the view field of the arthroscope 22. In this state, the switch 36 is operated to suitably perform the treatment to the treatment object region by use of the ultrasonic vibration.

Here, when the surgeon judges that a condition of a part of the cartilage 312a is Grade 2, the treating portion 68 of the ultrasonic treatment tool 32 is faced to a torn region of the cartilage 312a. Further, the torn region of the cartilage 312a is removed by transmitting the ultrasonic vibration to the treating portion 68 of the ultrasonic treatment tool 32. In addition, the bone spur formed in Grade 2 is removed by transmitting the ultrasonic vibration to the treating portion 68 of the ultrasonic treatment tool 32.

When the surgeon judges that the condition of a part of the cartilage 312a is Grade 3, the treating portion 68 of the ultrasonic treatment tool 32 is opposed to the torn region of the cartilage 312a and a torn region of the lateral epicondyle 322 of the humerus 312. Further, the torn region of the cartilage 312a and the torn region of the lateral epicondyle 322 of the humerus 312 are removed together with the osteophyte formed in the lateral epicondyle 322 of the humerus 312 and the like, by transmitting the ultrasonic vibration to the treating portion 68 of the ultrasonic treatment tool 32. In this case, an amplitude of an ultrasonic transducer in treating the torn region of the cartilage 312a adhered to the lateral epicondyle 322 of the humerus 312 may be different from an amplitude in treating the torn retion of the lateral epicondyle 322 of the humerus 312.

When the surgeon judges that the condition of a part of the cartilage 312a is Grade 4, the cartilage 312a might peel from the lateral epicondyle 322 of the humerus 312. In this case, when the bone under the cartilage 312a undergoes necrosis due to an interruption in circulation of blood or the like, the bone cartilage piece separates to be liberated as a loose body in the joint capsule 335. In addition, the loose body might be separated also from the cartilage 312a in the joint capsule 130. In such a case, the treating portion 68 of the ultrasonic treatment tool 32 is faced to the torn region of the cartilage 312a and the torn region of the lateral epicondyle 322 of the humerus 312. Further, the torn region of the cartilage 312a and the torn region of the lateral epicondyle 322 of the humerus 312 are removed together with the osteophyte formed in the lateral epicondyle 322 of the humerus 312, by transmitting the ultrasonic vibration to the treating portion 68 of the ultrasonic treatment tool 32. Also at this time, the cartilage 312a is smoothened, and the exposed lateral epicondyle 322 of the humerus 312 is smoothened. It is to be noted that the region (loose body) liberated from the cartilage 312a is sucked or curetted to be removed.

Thus, in accordance with the condition of damaged region of the cartilage 312a, the ultrasonic vibration is transmitted to the treating portion 68 of the ultrasonic treatment tool 32, to suitably dissect the cartilage 312a. The cartilage 312a is suitably dissected so that the elbow joint 300 can be smoothly moved.

Further, in the treatment of removing the cartilage, the radio frequency device (RF device) has been heretofore used in the cutting-off of the cartilage which is a soft tissue and the abrader burr has been heretofore used in the removing of the bone which is hard tissues. The abrader burr performs the cutting off by the periaxial rotation as described above, and hence, when the cartilage is cut off with the abrader burr, a cut-off surface of the cartilage tends to be made fluffy as shown in FIG. 10B. Consequently, when the cartilage is abraded with the abrader burr, it is difficult to smoothen the cut-off surface and it is easier to generate concave and convex areas in the excised region. In addition, when the cartilage 112a is cut off with the abrader burr, as shown in FIG. 10B, a corner 353 is formed between a removed surface 351 from which the cartilage is removed and each of non-removed surfaces 352 adjacent to the removed surface 351.

In addition, when a radio frequency device is used to remove the cartilage, heat is generated by a radio frequency current flowing through the cartilage. Consequently, as shown in FIG. 10C, there is the fear that the cartilage is invaded by heat.

Figure 10A:
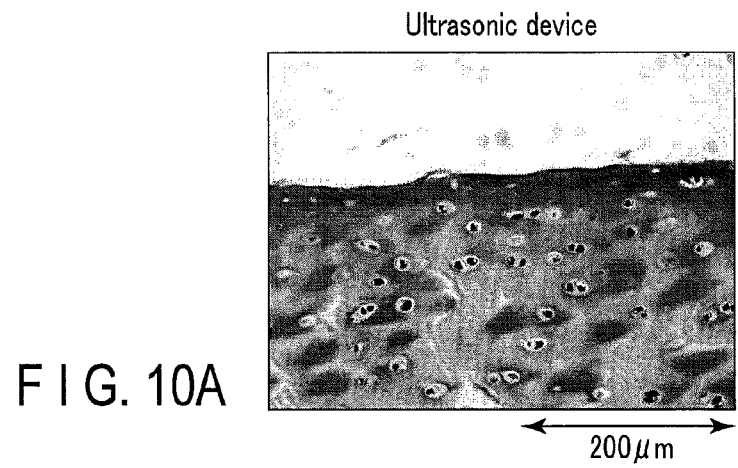
FIG. 10A is a schematic view showing, in the form of an enlarged and observed image, a state that the cartilage of the joint is cut off in the treating portion by use of the ultrasonic vibration transmitted to the treating portion of the ultrasonic treatment tool.
Figure 10B:
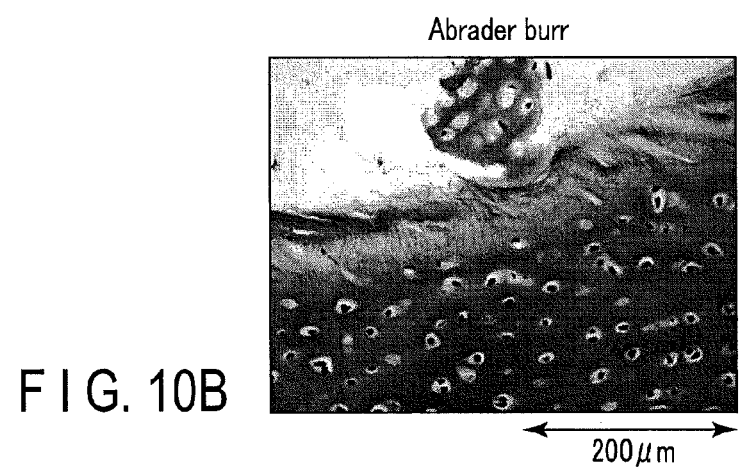
FIG. 10B is a schematic view showing, in the form of an enlarged and observed image, a state that the cartilage of the joint is cut off with the abrader burr.
Figure 10C:
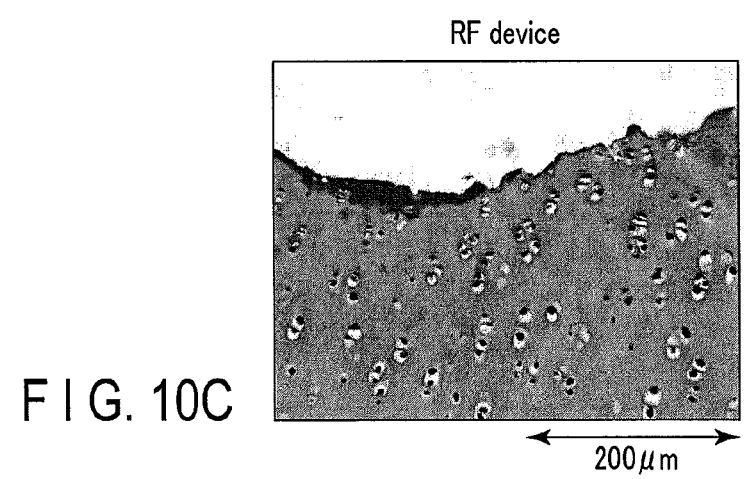
FIG. 10C is a schematic view showing, in the form of an enlarged and observed image, a state that the cartilage of the joint is cut off with an RF device.
Figure 11A:
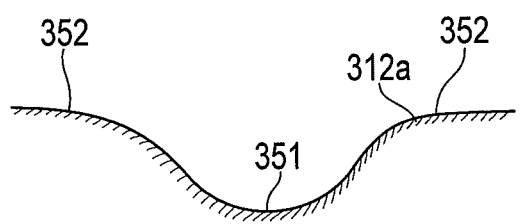
FIG. 11A is a schematic view showing, in a cross section, a removed surface cut off by use of an ultrasonic vibration in the treating portion of the ultrasonic treatment tool and a non-removed surface adjacent to the removed surface, in the cartilage of the elbow joint.
Figure 11B:
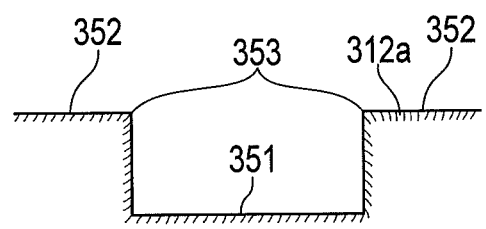
FIG. 11B is a schematic view showing, in a cross section, a removed surface cut off by an abrader burr and a non-removed surface adjacent to the removed surface, in the cartilage of the elbow joint.

On the other hand, in the case where the cartilage is cut off with the treating portion 68 of the ultrasonic treatment tool 32, as shown in FIG. 10A, a more precise and smoother cut-off surface can be formed than in the case where the abrader burr is used. In consequence, the excised region of the cartilage by the treating portion 68 of the ultrasonic treatment tool 32 has less concave and convex areas and is smoothened. In addition, when the cartilage is cut off with the ultrasonic treatment tool 32, as shown in FIG. 11A, a region between the removed surface 351 from which the cartilage is removed and each of the non-removed surfaces 352 adjacent to the removed surface 351 is continuous as a smooth surface in which any corners are not formed.

Further, the cartilage is cut off with the ultrasonic treatment tool 32 by use of the ultrasonic vibration, and hence the radio frequency current does not flow through the cartilage. Consequently, in the cartilage (312a) and the bone (lateral epicondyle 322 of the humerus 312) adjacent to the cartilage, a heat invasion is reduced, and thermal necrosis is prevented from being caused to the cartilages.

In addition, in the treatment of removing the cartilage, the cartilage (312a) and the bone (lateral epicondyle 322 of the humerus 312) are removed by use of the same ultrasonic treatment tool 32, and the treatment tool 32 does not have to be replaced with respect to the portal 304. Hence, the surgical treatment time can be shortened.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An elbow joint surgical treatment which is to be performed under an arthroscope, the surgical treatment comprising:
   inserting the arthroscope and a treating portion of an ultrasonic device into an elbow joint;
   excising a treated object region of a synovial membrane by transmitting an ultrasonic vibration to the treating portion in a state where the treating portion is in contact with the treated object region of the synovial membrane while observing the treating portion of the ultrasonic device and the treated object region of the synovial membrane with the arthroscope;
   bringing the treating portion of the ultrasonic device, used in excising the treated object region of the synovial membrane, to approach and come in contact with an osteophyte that is a treated object region positioned in one of a coronoid fossa of a humerus, an olecranon fossa of the humerus, a coronoid process of an ulna, and an olecranon; and
   removing the osteopyte by transmitting an ultrasonic vibration to the treating portion of the ultrasonic device in a state where the treating portion is in contact with the osteophyte while observing the treating portion and the osteophyte with the arthroscope.

2. The surgical treatment according to claim 1, wherein the ultrasonic vibrations of different amplitudes are transmitted to the treating portion of the ultrasonic device for use in excising the treated object region of the synovial membrane and removing the osteophyte.

3. The surgical treatment according to claim 2, wherein the amplitude of the ultrasonic vibration in excising the treated object region of the synovial membrane is smaller than the amplitude of the ultrasonic vibration in removing the osteophyte.

* * * * *